(12) United States Patent
Peterson et al.

(10) Patent No.: US 6,714,299 B2
(45) Date of Patent: Mar. 30, 2004

(54) USE OF LIGHT SCATTERING PARTICLES IN DESIGN, MANUFACTURE, AND QUALITY CONTROL OF SMALL VOLUME INSTRUMENTS, DEVICES, AND PROCESSES

(75) Inventors: Todd Peterson, Coronado, CA (US); Laurence Warden, Poway, CA (US); Juan Yguerabide, La Jolla, CA (US); Evangelina Yguerabide, La Jolla, CA (US)

(73) Assignee: Genicon Sciences Corporation, San Diego, CA (US)

( * ) Notice: Subject to any disclaimer, the term of this patent is extended or adjusted under 35 U.S.C. 154(b) by 0 days.

(21) Appl. No.: 09/906,580

(22) Filed: Jul. 13, 2001

(65) Prior Publication Data

US 2003/0020910 A1 Jan. 30, 2003

(51) Int. Cl.[7] .............................................. G01N 21/00
(52) U.S. Cl. ...................................................... 356/338
(58) Field of Search ................................ 356/337, 335, 356/336, 338, 339, 340, 341, 342, 343, 244

(56) References Cited

U.S. PATENT DOCUMENTS 6,180,415 B1 * 1/2001 Schultz et al. .............. 436/518
6,214,560 B1   4/2001 Yguerabide et al. ......... 435/7.1

FOREIGN PATENT DOCUMENTS

WO    WO 97/40181    10/1997
WO    WO 99/20789    4/1999

OTHER PUBLICATIONS

U.S. patent application Ser. No. 08/953,713, Yguerabide et al., filed Oct. 17, 1997.
Freemantle, M., "Downsizing Chemistry: Chemical Analysis And Synthesis On Microchips Promise A Variety Of Potential Benefits," Chemical and Engineering News, 77(8), 27–36 (1999).
Frens, G., Nature Physical Science, 241:20–22 (Jan. 1973).
Gale, B.K., Caldwell, K.D., Fraiser, A.B., "A Micromachined Electrical Field–Flow Fractionation ($\mu$EFFF) System", IEEE Transactions on Biomedical Engineering, vol. 45, No. 12, pp. 1459–1468 (Dec. 1998).
Schena, M., editor, "Microarray Biochip Technology," pp. 1–38, chapters 1 and 2, 2000, Eaton Publishing, MA.
Stevenson, P.C., "Some Experiments on Colloidal Gold", PhD. Thesis, Princeton University (1949).
Turkevitch, J., Stevenson, P.C., Hillier, J., Disc. Faraday Society, 11:55–75 (1951).
Zsigmondy–Thiessen, "Das Kolloide Gold," pp. 48–64, (1925).

* cited by examiner

*Primary Examiner*—Audrey Chang
*Assistant Examiner*—Denise S. Allen
(74) *Attorney, Agent, or Firm*—Jones Day

(57) ABSTRACT

The use of light scattering particles in the design, manufacturing, and quality control of microscale devices and process, and the analysis of solid substrate and porous substrate characteristics is described.

26 Claims, 3 Drawing Sheets

Narrow Field Detection

Wide Angle Detection

Time Lapse Images
RLS Particles in a Microchannel

USE OF LIGHT SCATTERING PARTICLES IN DESIGN, MANUFACTURE, AND QUALITY CONTROL OF SMALL VOLUME INSTRUMENTS, DEVICES, AND PROCESSES

BACKGROUND OF THE INVENTION

The present invention concerns the field of development and quality control of devices and materials for fluid handling, control, flow, and deposition.

At presen methods for analyses in these applications typically rely upon detection of fluorescent or chromogenic dyes using a time-lapse or high-speed video device. For flow analysis, a fine stream of the fluorescent or chromogenic detection agent can be introduced into the system. However, information obtained using these methods is of limited utility with respect to a significant area of the flow channel because of limited sensitivity and rapid diffusion and dilution of the detected agent.

Resonance light scattering (RLS) particles have been shown to provide highly sensitive labels in bioanalytical assays in a variety of different formats. Such uses are described, for example, in Yguerabide at al., PCT/US97/06584, Yguerabide et al., PCT/US98/23160, Yguerabide et al, U.S. application Ser. No. 08/844,217, now U.S. Pat. No. 6,214,560, and Yguerabide et al., U.S. application Ser. No. 08/953,713, and the patents and publications cited in the backgrounds thereof, all of which are hereby incorporated by reference herein in their entireties, including drawings.

Particles with similar composition have also been used in connection with electron microscopy and as cytological stains, utilizing their associated absorbence properties.

SUMMARY OF THE INVENTION

The present invention relates to the use of resonance light scattering (RLS) particles as tools to guide and refine design, manufacture, and quality control parameters in production of fluid-containing devices and processes. The use of such particles is particularly advantageous for small volume devices, such as micro, nano, and pico volume fluidic, capillary, or deposition instruments, devices, and products.

These applications of RLS particles relate to the capability provided by such particles to obtain detailed information associated with micro-scale, nano-scale, and pico-scale flow, as well as static properties or parameters, using appropriately formulated RLS particles. Such information can be readily obtained using simple instrumentation for detection, or even using detection by eye with appropriate magnification, though more complex apparatus, especially those having electronic analysis and/or control capabilities are advantageous in many applications.

Using such RLS particles, it is possible to detect light scattering from the particles continuously, without the bleaching experienced with fluorophores, and with very high sensitivity and signal stability. Detection can even be readily performed on single particles.

Thus, in a first aspect, the invention provides a method for determination of a dynamic property of a fluid volume. The dynamic property is determined by determining the distribution or location or both of at least one light scattering particle using detection of light scattered from the particle or particles in at least a portion of said fluid volume. For some devices it may be useful to view the particles in the entire device simultaneously, while in other cases, it may be useful to view only a portion of the device, e.g., a valve, flow channel, or mixing chamber. In still other cases, it may be advantageous to follow a particle or set of particles as they are transported through a device or portion of a device.

A variety of flow properties can be involved, and the determination can involve one or more than one such property, determined simultaneously or sequentially. For example, the dynamic property may be flow rate, or particle distribution. In certain embodiments, the particles are directly or indirectly attached to a biological molecule such as a nucleic acid molecule such as nucleic acid probe, a polypeptide such as an antibody or antibody fragment, a lectin, a carbohydrate, or a cell. Thus, the attached light scattering particle provides a method for determining the distribution of biological molecule or cell in a volume or on a surface. In preferred embodiments, the device is an array, or other device on which molecules are deposited or bound in a localized manner, e.g., spotted on a solid phase surface or deposited in a well.

Similarly, in preferred embodiments, the dynamic property is uniformity (or lack of uniformity) of drying on a solid surface. This is particularly applicable to development and quality control of arrays, e.g., nucleic acid or polypeptide arrays. Uniformity (or lack of uniformity) can be uniformity across discrete areas, where the areas are evaluated individually (though the individual evaluations can then be compared), thereby providing a larger scale evaluation or comparison). Examples of such discrete areas are the individual features on a planar array. Alternatively, the uniformity can be evaluated across multiple discrete areas. As an example, the number of functional probes bound in the various features on a planar array can be evaluated. In either type of evaluation, lack of uniformity is typically shown by a pattern to the particle distribution. Such a pattern may, for example, be irregular differences in concentration or density of RLS particle, or a gradient in such concentration or density across an area or volume. In such embodiments, the uniformity can be evaluated continuously, or at discrete times, or at endpoint, or in combinations.

In preferred embodiment, the deposited volume and/or number of features is as described for embodiments of other aspects involving arrays herein.

In another example, the dynamic property is a flow pattern in a device or portion of a device. For example, the device may be a multi-channel device. Such a flow pattern, can for example, be the distribution of particles across a flow channel, presence and/or size of eddies or turbulence zones, flow velocity in a portion of a device, or a flow velocity profile across a channel, chamber, or other device portion.

In yet another example, the dynamic property is fluid mixing. The fluid mixing may be evaluated in one or more portions or elements of a device, or throughout the entire device. For example, the portion may, for example, be a mixing chamber, a port, a flow channel, a pump, or a flow channel intersection or junction. Such fluid mixing (as well as flow patterns and other properties or parameters) can be evaluated as a function of device parameters and/or other process parameters. Such other process parameters include, for example, fluid type (e.g., identity of solvent), electrical conductivity of the fluid, presence or absence or amount of one or more dissolved or suspended species, and viscosity of the fluid.

In preferred embodiments, the device is a small volume device, which may, for example, be a micro volume device such as a microchannel device; a nano volume device; a pico volume device; an array chip, plate, or slide; a pump, a port; a valve; a spotting pin; a channel junction, or a jet head.

Device and process evaluations can also be performed in devices or portions of multiple devices that have fluid connection. In this way, interactions between devices in a system can be determined and adjusted in beneficial ways.

In another aspect, the invention provides a method for analyzing deposition characteristics of features (spots) on an array, or other surface arrangement. The method involves depositing at least one fluid volume on a portion of a solid substrate, where the fluid volume contains a plurality of light scattering particles, and detecting the light scattering particles by detecting light scattered from the particles. The distribution or number or both of the particles is indicative of the deposition characteristics. Alternatively, another molecule(s) can be deposited on the array or other surfaces to which light scattering particles can be directly or indirectly bound. Then the presence, amount, and/or distribution of the light scattering particles serves as an indicator of the presence, amount, and/or distribution of the deposited molecule(s). The determinations can also involve other deposition characteristics.

Preferably the array contains at least 5, 10, 50, 100, 200, 500, 1000, 5000, 10000 spots, or even more. In particular embodiments, the number of features on the array is within a range between any two of the feature numbers just provided, inclusive of the endpoints.

Various deposition characteristics of array spots or other spots on a solid phase may be evaluated using the present method. For example, the deposition characteristic can be uniformity (or non-uniformity) of deposition. The uniformity can, for example, be evaluated as a 2-dimensional distribution of particles within a spot or spots, or as a deposition volume, and/or the uniformity of particle number in deposited spots. The distribution of particles can, for example, be used as an indicator of the distribution of probe molecules in a deposited spot or spots. Likewise, the deposition characteristic can be a drying pattern, for example the distribution of probe molecules during drying of the spot or spots, or a distribution of an active moiety during and/or after post-spotting processing.

The determination of number and/or distribution of a molecule or other detectable item can involve assay of number and/or distribution of functional components. For example, target, probe, or other binding molecule (e.g., an antibody or oligonucleotide probe) can be deposited on a surface. Then a binding assay can be performed, utilizing light scattering particles as described, to determine the number and/or distribution of probe (or other) molecules that have a particular binding function (e.g., specific binding and/or binding strength). Such assays can likewise be used to determine binding kinetics, e.g., by monitoring binding on a surface over time and/or binding stability (e.g., by using conditions of a particular stringency, or a range of stringencies). Monitoring over time can, for example, be performed using time lapse or video techniques. In preferred embodiments, the deposition characteristic determined is, or is indicative of, functional binding, for example, in nucleic acid hybridization, protein-protein interaction, and ligand-receptor binding.

As used herein, the term "array" refers to a device having a solid phase surface which has a plurality of features in distinct, physical locations, typically separated by blank or empty areas. The "features" are locations where particular molecules, often biomolecules, are immobilized for conducting assays. In most current arrays, the immobilized molecules are probes that bind to target molecules in a sample or samples applied to the array. As used herein, the term "array" is used as a general term for any such device. As used herein, the term "array chip" refers to an array with a planar solid substrate with surface area of 1 in$^2$ or less; the term "array slide" refers to an array with a planar solid substrate with a surface area greater than 1 in$^2$ up to 4 in$^2$ inclusive; the term "array plate" refers to an array with a solid substrate with a generally planar surface. In some embodiments, the plate has depressions, e.g., wells, for containing liquids.

In connection with arrays, the terms "features" and "spots" are used synonymously. The features may, for example, be particular areas on a flat surface, wells, or channels (which may be oriented in a flat, viewing plane of the array, or end-on to a flat, viewing plane of the array). Preferably the features are particular locations on a flat surface, e.g., specific oligonucleotide or polypeptide-containing areas on a glass or plastic slide or chip.

In particular embodiments, the small volume deposited at one or more features is 1 pL to 100 nL, preferably 10 pL to 10 nL, more preferably 50 pL to 10 nL, still more preferably 50 pL to 1 nL. In additional particular embodiments, the small volume deposited is 50 pL to 500 pL, 50 pL to 200 pL, 10 pL to 200 pL, 10 nL to 200 nL, or 200 nL to 2 $\mu$L. Also in particular embodiments, the volume deposited is in a volume range described by taking any two different particular volumes just specified as the inclusive endpoints of the range.

As in the previous aspect, in preferred embodiments the array has at least 5, 10, 50, 100, 200, 500, 1000, 5000, 10,000 features, or even more, or the number of features is in a range described by taking any 2 different values, as described, as the endpoints of the range.

The invention also provides a method for analyzing fluid flow in at least a portion of a device, preferably in a small volume device, more preferably in a plurality of portions of a small volume device. The method involves inserting a suspension of light scattering particles in the device, illuminating the light scattering particles in a plurality of portions of the device, and detecting the presence of light scattering particles as an indication of the fluid flow. The flow can, for example, be continuous, stopped, or pulsatile flow.

The portion or device may be any that is appropriate for fluid flow that allows, or can be adapted to allow illumination of particles within or on the device or portion of interest. Thus, preferably the device has at least a portion that is exposed or transparent to light, preferably to visible wavelength light, preferably the incident light beam is provided by laser or collimated incident light beam.

In connection with flow devices and/or other fluid-containing devices, light scattering particles can also be used to monitor binding of molecules in solution to the interior walls of the device. In many cases, such binding is undesirable, for example, as it results in loss of a significant portion of sample or because it makes quantitation of material or process results problematic or questionable. In preferred embodiments, determination of binding can be carried out similarly to binding determinations on an exposed surface (e.g., on a microarray). For example, in an exemplary embodiment, the solution containing the molecule of interest is placed in or flowed through the device or portion of a device. Unbound material is washed out of the device or portion, and bound molecules are detected by directly or indirectly binding light scattering particles to the bound molecules and detecting the light scattering particles as an indication of the presence of the bound molecules.

Flow detection and analysis can be performed in various ways depending on the flow property or properties of interest. For example, time lapse imaging can be used to provide particle images at discrete time points, extended exposures can be used to provide trace lines showing particle paths, and video images can be used to provide moving particle images. Combinations and other options can also be used.

In addition, in another aspect, the invention provides a method for analyzing at least one surface characteristic of a solid substrate or porous matrix. The method involve detecting the distribution or number or both of the light scattering particles on at least a portion of the substrate, e.g., a surface, by detecting light scattered from the particles, following treatment of at least a portion of the substrate with at least one fluid volume containing a plurality of light scattering particles. The distribution or number or both of the particles is indicative of the characteristic.

As used herein in connection with suspensions of light scattering particles, the terms "treatment", treating" and words of like import refer to contacting a material or composition with the suspension, and can also include additional processes, for example, non-covalent binding, covalent binding, and washing.

In the context of substrate analysis, e.g., surface analysis, the terms "characteristic", "surface characteristic", and "matrix characteristic" refer to a physical, chemical, and/or electrical property of the solid substrate, e.g., texture, planarity, porosity, surface charge, surface charge uniformity, hydrophobicity, hydrophilicity, reactivity, and combinations thereof, as well as other properties. One of ordinary skill in the art will recognize that the characteristics that can be analyzed are those that affect the number and/or distribution of particles on the surface, either directly or indirectly (e.g., through another component that is attached or becomes attached, directly or indirectly, to the particles).

Thus, in preferred embodiments, the characteristics analyzed include one or more of surface on matrix uniformity, uniformity of one or more coatings, uniformity of charge, uniformity of hydrophilicity, uniformity of hydrophobicity, and uniformity of charge density. The characteristic can concern a surface or surfaces and/or substrate through at least a portion of a porous matrix.

The terms "hydrophobicity" and "hydrophilicity" have their usual technical meaning, referring to whether a material does not associate readily with water, or associates readily with water, respectively.

Also in preferred embodiments, the solid substrate is a glass substrate, a functionalized glass substrate, a plastic substrate, a silicon substrate, a membrane substrate, a metallic substrate, or combinations thereof.

The determination of light scattering particles on the surface can be performed with illumination and detection on the same side of the substrate, e.g., membrane (for either transparent or non-transparent membranes or other substrates) or from opposite sides (for essentially transparent membranes or other substrates, and substrates that can be made essentially transparent).

In the context of this invention, "membrane" refers to a thin, flexible impermeable or microporous material, preferably synthetic material. Preferably pores or channels in the membrane are no larger than 20 $\mu$m, more preferably no larger than 10, 5, 2, 1, 0.5, 0.2 or 0.1 $\mu$m, or in a range specified by any two of these specified endpoints. Preferably, a membrane is a uniform sheet of material with essentially uniform composition, e.g., a film, though in some embodiments a membrane is fibrous material, e.g., woven or matted fibrous material. Examples of commonly used materials include nylon, nitrocellulose, polyvinylidene fluoride (PVDF), and cellulose.

As used herein, the term "matrix" or "matrix material" refers to a porous material, preferably a microporous material. A porous material is one with channels that allow entry or passage of fluid and/or air. Such channels may be discrete or interconnecting, and may be through channels and/or blind channels, but are preferably through channels. Preferably such passages are of sufficient size to allow entry or passage of light scattering particles of at least 1 nm diameter, more preferably at least 10, 20, 30, 40, 60, 80, 100, 120, or 150 nm. Preferably the channels are, on average, at least 50, 100, 200, 400, 600, 800, or 1000 nm in cross-section. The degree of porosity can vary, e.g., representing at least 1, 2, 5, 10, 20, 40, or 50% or even more of a surface of a material. Thus, matrix materials include such exemplary materials and items as membrane filters, fibrous filters, and sintered glass filters.

The term "functionalized" refers to a chemical modification that prepares a material, e.g., a glass, plastic or metal surface for subsequent chemical interaction by attaching or creating suitable functional groups or moieties. Thus, for example, an analysis can determine the number and/or density of accessible groups on a surface after functionalization.

As used herein, the term "fluid" refers to a material or combination of materials that is liquid under the relevant pressure and temperature conditions, e.g., at room temperature and one atmosphere.

In the context of this invention, the term "device" means an article of manufacture that includes one or more channels or reservoirs or locations for fluid to be present, e.g., for flow or deposition.

The term "microchannel" refers to a channel of sufficient size to allow fluid flow, preferably a channel generally in the form of a tube, that has mean cross-sectional measurement of 3 mm or less. In particular, embodiments the channel is 2 mm or 1 mm or less, or 0.5 mm or less, or 100 $\mu$m or less, preferably 10 $\mu$m or less or 100 $\mu$m or less, still more preferably 80 nm or less, or 60 nm or less, or 40 nm or less, or 20 nm or less.

"Microscale" refers to devices or portions of devices or processes with dimensions of 3 mm or less, preferably 1000 $\mu$m or less, generally in the range of 1–500 $\mu$m, for functional parts or processes. Thus, channels, junctions and the like are typically of such dimensions.

"Nanoscale" refers to devices or portions of devices or processes with dimensions of 1000 nm or less, generally in the range of 1–500 nm, for functional parts or processes. Thus, channels, junctions, and the like are typically of such dimensions.

"Microfluid dynamics" refers to the fluid dynamics in microscale systems, preferably in systems with flow channel dimensions of 1 mm or less, 500 $\mu$m or less, 100 $\mu$m or less, 500 nm or less, 100 nm or less, 50 nm or less, or even smaller. Thus the term refers to the fluid behavior in such channels.

The term "subfluidic region" refers to a portion of a flow channel or reservoir. Generally the term is used in connection with the behavior of fluids in such a sub-region in connection with microscale or nanoscale processes or channels or reservoirs. Likewise, the term "sub-flow pattern" refers to the fluid flow pattern or behavior in a sub-region of a flow channel or reservoir, generally microscale or nanoscale. Such regions and flows can be monitored using the methods of the present invention.

"Microfabrication" refers to the techniques and processes of producing a microscale or nanoscale device. Exemplary techniques include photoetching, laser shaping, micromachining, and the like. The method utilized will depend on factors such as the scale and the materials being utilized.

The term "fluid deposition" refers to the process of placing a volume, generally a small volume, on a solid phase surface. The deposition may, for example, be on a flat surface, or in a depression, or cavity in the surface, or on the walls of a tube through a solid phase material. Exemplary methods include those commonly used for producing microarrays. A variety of such deposition methods, as well as other factors in production of arrays, are described in *Microarray Biochip Technology*, Mark Schena, ed., Eaton Publishing, Nattick, Mass., 2000, and are applicable for the present methods. Deposition methods include, for example, piezoelectric, inkjet, solenoid/piston, and pin spotting. Deposited volumes are preferably 1 $\mu$L or less, 0.5 $\mu$L or less, 0.1 $\mu$L or less, or more preferably 10 nL (nanoliters) or 1 nL or less, or even 500 pL (picoliters) or less, 200 pL or less, 100 pL or less, or 50 pL or less.

The term "small volume" as used herein refers to a volume of 10 mL or less, preferably 5 mL or less or 1, 0.5, 0.1 mL or less, more preferably 10 $\mu$L or less, or 1, 0.5, 0.1 $\mu$L or less, still more preferably 10 nL, 1 nL, 0.5 nL, or 0.1 nL or less. Still smaller volumes are also included. Thus, a small-volume device has a volume within the device within the limits described. The term may also be used in connection with portions of a device, or a process, or sub-process.

"Microvolume" refers to volumes of equal to or less than 1000 $\mu$l, generally in the range of 1 to 1000 $\mu$l; in exemplary embodiments 100–1000 $\mu$l, 200–800 $\mu$l, 100–500 $\mu$l, 1–500 $\mu$l, 800 $\mu$l or less, 500 $\mu$l or less, or 200 $\mu$l or less.

"Nanovolume" refers to volumes of 1000 nL or less, generally in the range of 1 to 1000 nL, in exemplary embodiments 1–600 nL, 1–400 nL, 100–1000 nL, 100–600 nL, 800 nL or less, 500 nL or less, or 200 nL or less.

"Picovolume" refers to volumes of 1000 pL or less, generally in the range of 1 to 1000 pL, in exemplary embodiments, 1–600 pL, 1–400 pL, 100–1000 pL, 100–600 pL, 800 pL or less, 500 pL or less, or 200 pL or less.

"Resonance light scattering particles" (RLS particles) refers to particles that elastically scatter incident light with high efficiency. Preferably the particles are metal or metal-like particles. Preferred examples include gold particles, silver particles, and mixed composition gold and silver particles as well as particles containing at least 1, 5, 10, 25, 50, or 5% by weight of gold or silver or a combination of gold and silver. Examples of mixed composition particles are particles with silver surrounding a gold core, and gold over silver. For silver particles, a thin outer layer of gold can be advantageous, e.g. by providing light scattering characteristics of a silver particle while stabilizing the particle with the gold outer layer. Particles are also included that contain or are composed of other materials that have sufficient light scattering intensity to allow use as labels or as flow markers, preferably with particles sizes of 1–500 nm.

The size of RLS particles can be selected as needed or useful for particular applications. For example, particles can be selected to provide different colors on scattering of white, or more generally polychromatic light. Likewise, it may be beneficial to select particles of a particular sizes or with certain size limitations based on the dimensions of the fluid-containing portions of the device. In many cases, it is preferable to utilize particles that are small compared to the dimensions of the fluid channel or chamber, e.g., $\leq \frac{1}{5}$, $\frac{1}{10}$, or $\frac{1}{20}^{th}$. In many applications such size limitations are useful so that that particles will move freely through the device, and preferably will respond to eddies, turbulence, and other sub-features of the flow in the device to allow determination of those characteristics.

By "metal-like" particles is meant any particle or particle-like substance that is composed of metal, metal compounds, metal oxides, semiconductor (SC), superconductor, or a particle that is composed of a mixed composition containing at least 0.1% by weight of metal, metal compound, metal oxide, semiconductor, or superconductor material.

By "coated" particle is meant a particle has on its surface a layer of additional material. The layer is there to chemically stabilize the particle in different environments, and/or to bind specific molecules by molecular recognition means. Such coatings include, for example, inorganic and organic compounds, polymers, proteins, peptides, hormones, antibodies, nucleic acids, receptors, and the like. As described in the Yguerabide references cited herein, coated metal-like particles have similar light scattering properties as compared to uncoated metal-like particles, both of which have superior light scattering properties as compared to non-metal-like particles.

By "non-metal-like" particles is meant particles that are not composed of metal, metal compounds, superconductor, metal oxides, semiconductor, or mixed compositions that are not composed of at least 0.1% by weight of metal, metal compound, metal oxide, superconductor, or semiconductor material.

In this invention, it may be advantageous to provide a plurality of different particles, where each of the plurality is separately distinguishable. The plurality of different particles means that there is one or more individual particles, generally a large number of individual particles, of each of the different, separately distinguishable particles. The composition, size, and shape of the particles are chosen to provide distinguishable light scattering particles, e.g., different colors and/or different intensities. For example, roughly spherical gold particles of 40, 60, and 80 nm diameter can be used to provide distinguishable colors when illuminated with white (or polychromatic) light. In particular embodiments, 2, 3, 4, 5, 6, or even more distinguishable particles are used. The plurality of different particles can, for example, be used to analyze mixing of fluids from two different sources, e.g., from two different channels within a device, or to visualize the mixing of a small volume as it is combined with a larger volume. Such different particles can be provided, for example, using gold particles of different sizes, and/or silver particles of suitable size to provide distinguishable colors (e.g., two or more of 40, 60, and 80 nm gold particles, and 40 nm silver particles. Those skilled in the art will recognize a variety of other applications for multiple distinguishable particles.

Also, non-spherical particles may be used to provide useful information on flow or fluid properties, e.g., flow rate, viscosity, turbulence, flow gradients, and the like. Non-spherical particles that are elongated, e.g., particles that are generally oval or rod-shaped, can be distinguished from generally spherical particles by flickering in the scattered light as they rotate. Thus, the observable flickering will correlate with the flow properties, such as those listed above, e.g., by reduction in the flicker rate as viscosity increases. Thus, such elongated particles will provide additional characterization of flow properties in a system or device.

Preferably, but not necessarily, the detection of light scattering in the present methods is performed using simple instrumentation. By simple instrumentation is meant with magnification less than 500×, and without confocal imaging, and preferably without use of laser illumination. However, in some embodiments, laser illumination is advantageous, as laser may have important applications in providing incident light precision. Use of laser illumination can readily be used with sets of particles selected to provide multiple distinguishable characteristics, e.g., distinguishable intensities, distinguishing 2 or more different particles. Typically the sets of particles are selected by size and/or composition to provide the distinguishable characteristics. However, in some embodiments, it will be beneficial to use such apparatus, and/or to use electronic imaging devices. In addition, electronic image processing and analysis tools can also be used.

The term "dynamic property" refers to a property or characteristic of a system or material that changes over time. The property may, however, reach an endpoint. Examples include, without limitation, flow rate, mixing, distribution of a material, distribution of material during drying, and binding, distribution and/or number of function molecules or components, stability of material on a surface (e.g., as a function of experimental processing), presence of flow features such as turbulence or micro eddies or other extremely local flow dynamic effects. In particular embodiments, one or more of these dynamic properties is determined, at one or more timepoints or continuously over a time interval(s)

Detection may be performed using any of a variety of different detectors. One of ordinary skill in the art will be familiar with numerous detectors. For example, in some applications it may be sufficient for the particles to be viewed by eye. However, in other applications it may be preferable to use a film or electronic detector (e.g., a film or electronic camera), that produces a picture and/or electronic record. Such cameras may be still (which may be used in time-lapse manner) or video cameras. The film or electronic image can be further processed and/or analyzed to identify features (e.g., the number and/or position of particles) and/or to characterize one or more properties of such features. Of course, video cameras may be used with frame-grabbers to allow single or multiple image processing and/or analysis. Electronic cameras include, for example, charge coupled device (CCD) cameras, charge injection device (CID) cameras, and Complementary Metal Oxide Semiconductor (CMOS) cameras.

While the description of aspects and embodiments herein is generally presented in terms of fluids (used herein as equivalent to the term liquids), the analysis of flow behavior using RLS particles can also be performed in gaseous flow, e.g., air flow. Typically, but not necessarily, the velocities in such flow are greater than for liquids. Also typically, RLS particles used for gas flow analysis will be small, e.g., 1–40 nm, preferably 1–20 or 1–10 nm. In some applications it is also beneficial to use particles of lower density than solid metal particles. Examples include particles with a metal shell over a low density core, thereby maintaining high light scattering intensity but enhancing the ability of the particle to remain suspended in the gas for a useful period of time. The detection and analysis of particle distribution, flow pattern, and other properties in gas systems is essentially the same as for the fluidic systems described herein, and are part of the present invention.

Additional aspects and embodiments will be apparent from the following Description of the Preferred Embodiments and from the claims.

DETAILED DESCRIPTION OF THE PREFERRED EMBODIMENTS

Figure 1:
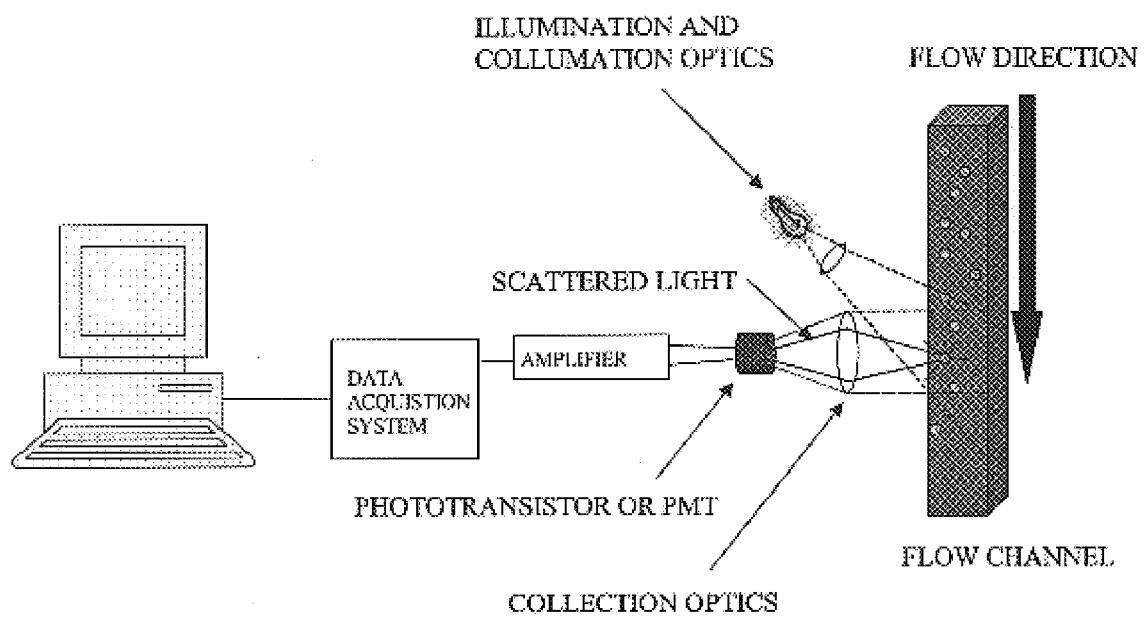
FIG. 1 is a schematic illustration of a system arranged for detecting light scattering particles in a flow device using a narrow detection field, with electronic detection and data acquisition, and with a computer for data storage and/or data processing.

The present invention concerns the use of resonance light scattering (RLS) particles in connection with small volume devices and processes, e.g., in the design, manufacture, and quality control of small volume devices and instruments. Individual RLS particles of appropriate size and composition can be detected using simple instrumentation, or by eye with appropriate magnification. This capability provides many applications for the use of RLS particles in industrial production of micro and nano volume fluidic, capillary or deposition instruments, devices and other products.

In particular, this invention concerns the ability to obtain detailed and specific information associated with micro-scale, nano-scale, and pico-scale flow and suspended and attached material distribution using appropriately formulated RLS particles, even with simple instrumentation.

Current methods for such analyses typically rely upon detection of fluorescent or chromogenic dyes using a time-lapse or high-speed video device. In flow systems, a fine stream of the detection agent may be used for introduction into the system. However, information obtained using these methods is of limited utility with respect to a significant area of the flow channel because of limited sensitivity and rapid diffusion and dilution of the detected agent.

In contrast RLS particles are highly intense and particulate in nature. Using properly formulated RLS particles under essentially the same conditions, one can observe and measure flow patterns, e.g., micro-flow and nano-flow patterns, under various experimental and applied run conditions over extended distance and time, as well as binding properties, deposition characteristics, and other properties.

In micro-, nano-, and pico-scale deposition applications, RLS particles possess properties that provide important advantages over current methods that largely rely upon fluorophores or isotopes. In these methods, the inability of fluorescent dyes to maintain a strong, non-diffuse, and consistent signal limits the utility of these detection agents. In contrast, RLS particles provide an important tool for observation and measurement of fluid distribution and uniformity during deposition and drying at high resolution. RLS particles also provide better precision and sub-fluidic resolution. Again, simple instrumentation, such as a conventional laboratory microscope unit with time lapse video may be used. Many other instrument configurations can also be used.

Thus, RLS particles can be formulated for and used in any application in which direct visualization, and qualitative and/or quantitative measurement of distribution or flow properties of small liquid volumes and/or suspended or attached components is desired. The inherent stable intensity and particulate nature of RLS particles make them ideal for such applications as they provide a quantifiable (individual particle counting and/or integrated intensity), stable signal that does not diffuse. Another aspect of the invention is the production and formulation of RLS particles for optimal performance in a particular micro-volume deposition or flow application. Exemplary applications of these particles are provided below, but are not intended to be limiting to the invention.

While RLS particles are particularly useful for very small volume devices, such particles can also be used in connection with larger volume devices and processes, e.g., in the design and testing of larger pumps and other flow system components.

As indicated above, Yguerabide at al., PCT/US97/06584, Yguerabide et al., PCT/US98/23160, and Yguerabide et al, U.S. Pat. No. 6,214,560 all describe a large number of different options for particles, particle coatings, binding of molecules to particles, and method and apparatus for detecting particles by light scattering. All of the information provided therein can be utilized in embodiments of the present invention.

Preparation of RLS Particles

A large number of different methods for preparing light scattering particles of different compositions and different sizes have been described and can be used in the present methods. Examples of such methods are provided in Yguerabide PCT/US98/23160, WO 99/20789; Frens, *Nature Physical Science* 241: January (1973); Frens, et al., *Kolloid-Z. u. Z. Polymere* 250:736–741 (1972); Turkevitch, et al., *Diss. Faraday Soc.* 11:55–75 (1951); and Stevenson, "Some Experiments on Colloidal Gold", Ph.D. Thesis, Princeton University (1949). Exemplary preferred particles are gold and silver particles, or particles composed of gold and silver, or gold and silver in combination with one or more other metals and/or one or more other materials. Particles can also be size fractionated to provide particular size ranges for particles. This fractionation is advantageous, for example, for discrimination of different size particles.

For example, a particle growing procedure can be utilized that involves first making a preparation of "seed" gold particles which is then followed by taking the "seed" particle preparation and "growing" different size gold (see Examples 1 and 4) or silver particles (see Example 3) by chemical methods. For example, 16 nm diameter gold particles are used as the "seed" particles and larger diameter gold particles are made by adding the appropriate reagents (see Example 4). This is also useful for making mixed-composition particles.

It is also advantageous to stabilize the particles, e.g., against clumping or precipitation. This can be done, for example, by coating the particles with another substance that enhances their stability. A variety of such coatings are described in the Yguerabide applications referenced above. Coating in the present case may also reduce or eliminate non-specific particle binding to the micro or nano flow device surfaces in cases where that is advantageous.

While gold particles can advantageously be used in the present methods, other types of RLS particles can also be used. For example, silver particles provide intense light scattering and are used in embodiments of the present invention.

Detection of Light Scattering Particles

For the applications of this invention, light scattering particles are commonly detected in solution, although the detection can also include particles bound on a surface, e.g., for determination of array spot or feature drying characteristics or binding distributions. Suitable apparatus for such detection can be of many different types and configurations. A variety of useful detection methods are described, for example, in Yguerabide at al., PCT/US97/06584, WO 97/40181; Yguerabide et al., PCT/US98/23160, WO 99/20789; Yguerabide et al, U.S. Pat. No. 6,214,560; and U.S. application Yguerabide et al., Ser. No. 08/953,713. In general, a variety of different light sources can be used, for example, incandescent lamps, light emitting diodes, lasers, polarized light sources (e.g., linearly polarized), continuous sources, and pulsed sources.

The illumination beam is directed toward the light scattering particles to be detected. The light can be transmitted directly or can be guided through a light guide, such as a prism or optical fiber.

The light scattered from the particles can be detected in various ways, including, for example, by unaided eye, by eye through a light microscope (e.g., using magnification of 1–100×, 50–200×, 100–500×, or 500–1000×), with a still camera (analog or digital), with a video camera, with a photodiode or photodiode array, or with one or more photomultiplier tubes, or with combinations thereof.

While the brightness of the light scattered from particles such as gold or silver particles is sufficiently intense to allow detection under a wide range of conditions, including conditions with much more background light than optimal, it is preferable to arrange the illumination and detection apparatus to minimize background light. Thus, in order to increase sensitivity of detection, preferably techniques described in the Yguerabide et al. patent and applications cited above are utilized. For example, preferably the detector is positioned to reduce the amount of reflected light that enters the light collection components. Preferably the illumination source and detector are arranged to avoid detection at the direct illumination beam and to minimize detection of reflected and refracted light. Other exemplary techniques include the use of spatial filters to reduce stray light, band-pass filters to enhance sensitivity, use of laser or highly collimated light sources, and use of refractive index matching or other refractive index enhancement techniques. Such refractive index enhancement methods involve the selection or manipulation of the refractive index of media containing or covering the particles, or otherwise covering a surface or surfaces that would otherwise contribute to background light scattering, to reduce background light scattering and/or to enhance the light scattering from the particles used for detection (and/or to reduce the light scattering from other system components such as other particles in suspension).

Two different exemplary methods and associated apparatus are described here that can be selected depending on the design of the device to be monitored. If the device accommodates a narrowing of the flow into a channel of <10 $\mu$m or so, a simple detection system composed of a collimated light source and an area sensor such as a photomultiplier tube or PMT, or phototransistor. The detection sensor is preferably placed behind a lens system to focus the scattered light on the surface of the detector. The entire detection system is placed at an angle to the light source so as to create a darkfield illumination condition, thereby keeping unwanted light from entering the collection optics. (See, e.g., FIG. 1). The angle of both the illumination and detection are preferably optimized to achieve the maximum scattering signal from the particles, with minimum background contribution from the illumination. In this approach, an average signal is delivered to an interfaced computer of the entire field of view containing individual or multiple particles. The intensity of the signal from the detector is directly proportional to the number of particles in the field of view (assuming the system is operated within the dynamic range of the detection system). In order to calculate particles per unit volume in a dynamic system with continuous flow, the flow rate is controlled and factored with the detection signal to calculate particles per unit given volume of flow.

Figure 2:
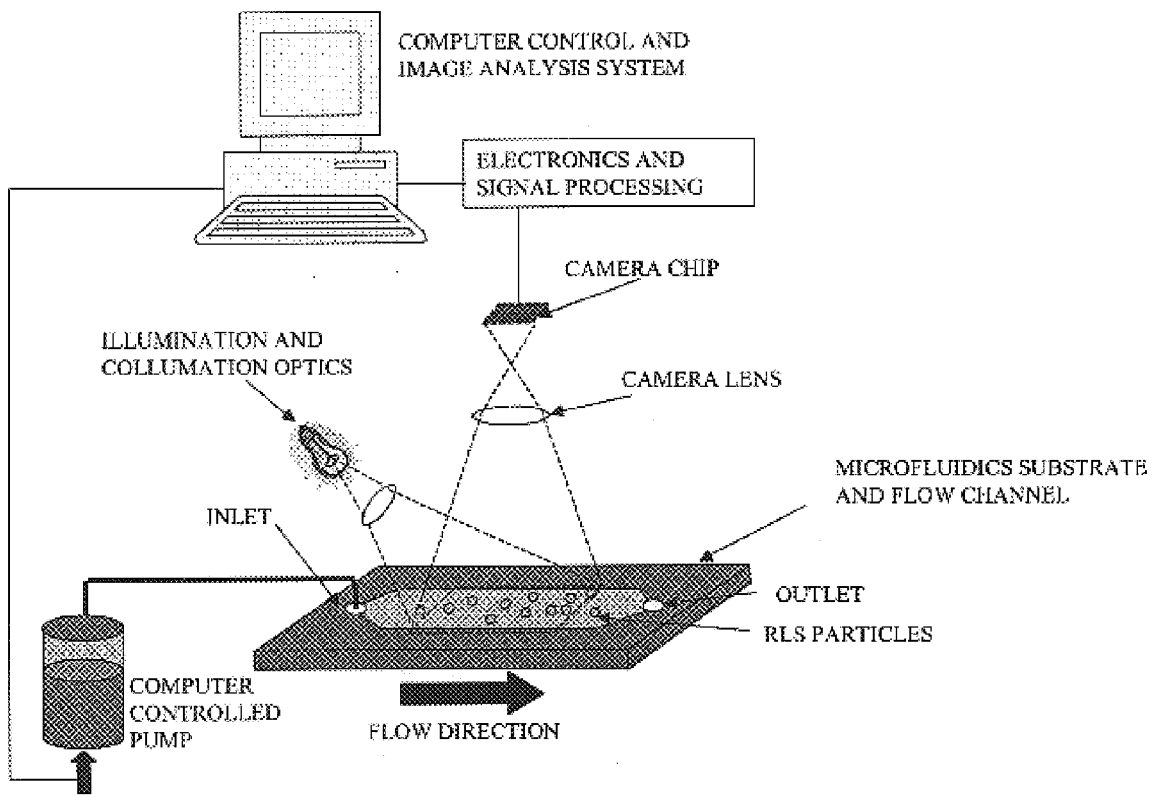
FIG. 2 is a schematic illustration of a system arranged for detecting light scattering particles in a flow device using a wide angle detection field, with electronic detection and data acquisition, and with a computer for data storage and data processing.

A second embodiment is particularly applicable to devices in which a narrowing of the flow path was not possible or if more accurate counting were desired. (See, e.g., FIG. 2) In this design, the illumination is a broader beam, e.g., across the entire channel. A high frame rate camera and lens is positioned over the channel. For coverage of the entire channel, the limit on channel width is dependant on the resolution of the camera and the size of the particle. Software processes the streaming images, counting and/or tracking individual particles from the point of entry into the camera frame until they move out of view. CMOS camera sensors are being produced with very high frame rates and built-in logic for detection and quantitation of moving objects in the field of view. Such cameras are suitable for the present use, but other cameras can also be utilized. Illumination is configured in a darkfield arrangement similar to the previous embodiment. With suitably sized view fields, the detection is not limited to a single channel, but can cover a larger portion of a device, even included an entire device.

Of course, many other configurations can be constructed and utilized, depending on the particular application. Examples include arrangements for detecting RLS particles at multiple view planes (e.g., 2 or 3 parallel view planes at different depths in a fluid), detecting from multiple directions (e.g., 2 or 3 dimensions), tracking particles through as device by moving the device in the field of view or moving the field of view over the device (e.g., to maintain particular particles within the field of view), and detecting particles of multiple locations within a device or in connected devices (e.g., 2, 3, 4, or more locations), as well as combinations of these.

Microfluidic systems

RLS particles can be used for many applications with microfluidic systems and devices. Some device examples are reviewed in *Chemical & Engineering News*, 77(8), 27–36, 1999. Further examples are well-known to those of ordinary skill in the art. Such devices are used for a variety of "lab on a chip" applications, among others, including drug screening, diagnostics, chromatography, and microeletrical field flow fractionation. Exemplary, non-limiting uses of RLS particles in microfluidic systems are briefly described below.

Microfluidic devices can be constructed in a variety of ways. One example is to use a micromachining process involving etching of a silicon substrate. The etched silicon can be sealed with glass to complete the channels and chambers. The fluidic connections can then be made at the edges of the device. Typically in such devices, flow channels are greater than 5 $\mu$m wide and elements are 0.5 $\mu$m to 200 $\mu$m deep.

Other methods of manufacture of microfluidic devices involve photolithography of a thin plastic layer deposited onto a glass or silicon substrate. In yet another technique, plastic injection molded parts can be fabricated with very small channels, and assembled into microfluidics devices using ultrasonic or solvent welding techniques.

Commonly, flow in microfluidics devices is low Reynolds number flow, such that $R_e$ is much less than one. The result is that there is often little turbulence. However, with such small dimensions, diffusion becomes a very significant factor. Still, an advantage offered by microfluidics is that, due to the very small fluid volumes involved and the resulting low inertias, flow can be reversed, or otherwise switched very fast. For example, flow can be switched at a junction by changing the applied fluid pressure, with the switching having been accomplished in as little as 20 msec. A potential complication is that microfluidic devices have low volume/surface ratios. Consequently, the ratio of molecules in solution to molecules adhering to a surface can be substantially lower than in large volume devices. If this is found to create difficulties, it can be addressed by coating the particles and/or the device surface to reduce the interaction.

Micro Fluid Dynamics

RLS particles allow one to directly measure individual and specified grouped sub-fluidic regions and components that function in microfluidic devices. Practical application of fluid dynamics in microflow environments has indicated an important balance between flow rate, flow pressure, fluid viscosity, channel dimension, channel material, and channel friction as important for optimal performance. In design and testing of any micro fluidic system, the ability to obtain vivid, real time measurement of flow and sub-flow patterns throughout the entire micro-channel system offers a tremendous advantage. For such analysis, current methods must treat regions of individual micro-channels as independent units instead of as components in an integrated system. As an example of the advantages provided by the present invention, flow dynamics in one micro-channel junction can be explored in conjunction with the flow dynamics of a feeder valve several channels away. Similarly, RLS particles can be used to design and test channel junctions and channel design configurations to optimize mixing or distribution of reaction components. Here again, RLS particles offer an advantage over existing approaches for obtaining useful information on component interaction, dynamics, and mixing across an integrated fluidic system.

Use of RLS Particles for Design and QC of Microfluidic Channels/Devices

Given their intense and non-diffusing signal generating power, RLS particles provide an excellent tool for guiding the design and performing quality control of microfluidic channels and associated devices. RLS particles used for these applications offer superior and quantifiable measurement of localized fluid dynamics in comparison to fluorescent dyes and other typically used fluid-dynamic label systems. In this application, RLS particles are introduced into microfluidic channels and hydrodynamic flow is visually monitored using appropriately configured illumination and detection optic instrumentation and software. Flow rates and microflow patterns can be determined by measuring and/or visualizing the particle flux across desired channel volumes, areas or dimensions.

Thus, RLS particles can be used to optimize channel design and manufacturing processes to meet the fluid dynamic requirements of the microfluidic device. This approach is not limited to analysis of various microfluidic channel designs per se, as flow properties of other associated flow device elements not limited to pumps, injection ports, valves, channel junctions and mixing stations can be similarly investigated. In addition, one can use RLS particles to study laminar fluid dynamics or microchannel surfaces of various character including fabricated or deposited electrode materials or other surface coatings.

In addition or in combination with evaluating flow characteristics, e.g., evaluating the effects of changes to the shape and/or material of the device, the present RLS particle methods can be used to evaluate the effects of fluid characteristics, either alone or in combination with evaluating device parameters. In particular applications, this is useful for microchannel devices. Such fluid characteristics can, for example, include viscosity, solvent, electrical conductivity, identity of dissolved molecules, and pressure, and combinations of these. As an example, the dispersion of a sample volume or reagent volume can be monitored as a function of sample (or reagent solution) viscosity and/or bulk solution viscosity. Likewise, in binding applications, the binding kinetics can be monitored as a function of solution viscosity. Monitoring both fluid characteristic and device characteristic effects allows co-optimization of a system, or identification of advantageous compromises, e.g., compromises in design and process that allow extended operating range. Many other specific applications will be apparent to one of ordinary skill in the art.

Microfabrication

RLS particles can be used as tools to aid microfabrication methods for the design, production, testing, and quality control of microfluidic devices and systems. For example, using RLS particles one can study and optimize an entire micro fluidic system, including, for example, microcirculation devices, micropumps, micropump controllers, microchannel sensors, microsensors and associated actuators, microchambers, microelectrodes, and the like, as an integrated system. This offers distinct advantages for system design and testing. These applications may include optimization of methods for design, engineering, manufacture, and/or testing microchannels. RLS particles allow one to rapidly design, product, and test microchannels made in any of various ways and various dimensions, if derived, rapidly and quantitatively.

For particular microflow applications, RLS particles can further be used to optimize production processes and flow properties of microchannels coated with various components. For example, in "lab on a chip" applications, RLS particles can be used to rapidly test formulations, methods, and performance of coatings that affect particular steps, such as binding or release of molecules in an analysis process. RLS particles can also be used for the design, testing, and production of "flow-through" chips that feature specifically immobilized probes, for example, in porous silicon wafers. Refractive index matching is preferably used to reduce background scattered light in such applications.

Fluid Deposition Systems

RLS particles can be used for detailed study of the properties and dynamics of small liquid volumes on solid surfaces. Whereas this is particularly the case in the rapidly growing field of microarray analysis, the use of RLS particles can be applied to other solid phase systems. This invention provides applications to microarrays although use of RLS particles to study properties and dynamics of small liquid volumes on solid surfaces is not limited to array applications.

Exemplary Description of how RLS Particles are Used for Determining Array Spotting Formulations and Processes The intense signal obtained from both individual RLS particles and a population of RLS particles on a surface, when observed and measured as integrated intensity, enables one to visually determine the distribution and homogeneity of deposited nucleic acids or proteins with an unprecedented level of ease, precision and resolution.

Experimentally, for example, one can determine the surface distribution of a deposited biomolecule on a glass slide, polystyrene or other plastic surface, or on membrane substrates such as nitrocellulose, PVDF or nylon by the following steps: Deposit and bind the biomolecule(s) to the surface or substrate, treat the surface or substrate with a blocking agent to prevent non-specific binding of RLS particles, react appropriately derivatized RLS particles with the surface or substrate under conditions that affect specific binding of the RLS particles to the deposited biomolecules, wash away RLS particles that are not specifically bound to the deposited biomolecules, and measure the morphology and surface distribution properties of the deposited biomolecules on the surface or substrate under appropriate RLS illumination and detection conditions. Membrane substrates in the systems above are generally made transparent by refractive index matching or other methods prior to viewing or quantitating.

In addition, one can also determine the distribution of the RLS signal in a functional test wherein the prepared slide or substrate has experimentally undergone defined hybridization, antibody binding, ligand-receptor binding, or other binding and wash conditions. In this case, monitoring the distribution of RLS signal provides a means to determine the distribution of functional biomolecules (i.e. biomolecules deposited in a manner that facilitates and permits stable cognate target binding) within the defined array feature.

Examples of this approach are provided below.

Microarrays

Microarray technology has revolutionized the analysis of gene expression and DNA sequence and protein detection and association by allowing one to analyze the binding of biomolecules present in a sample in a highly multi-parallel manner. Microarrays have become the central tool to explore the function of the genome and understand biological function. Large sets of individual proteins or gene probes are "spotted" onto solid surfaces and interrogated with analytes (targets) in a prepared sample. Quantitation of target binding data obtained allows one to acquire a tremendous amount of information for a large number of genes simultaneously. This approach has greatly accelerated the study and understanding of biological systems.

Currently, several methods are widely employed to deposit nucleic acid or protein onto solid surfaces in production of microarrays, including pin transfer, syringe-solenoid and piezoelectric. These methods generally transfer between 250 and 10 nL per spot, although smaller volumes are possible (and would probably be more widely used if not for limited detection sensitivity and detector resolution limitations) with the latter two methods. In all cases, a small volume of fluid containing the desired probe is applied to the surface.

Surfaces for deposition are often derivatized glass microscope slides, although other substrates, including plastic or membrane surfaces have also been used. Once deposited, the small liquid volume generally dries on the surface over a brief period of time. In some cases, application of the small liquid volume containing the desired probe takes place in a controlled humidity environment. This allows the target to interact more extensively with the glass substrate by remaining for a longer time in the liquid state. The method of spotting should generally be developed in concert with binding and detection aspects of the array system. Current methods to examine deposition of small liquid volumes on arrays include isotopic (generally $^{33}P$ or $^{32}P$) or fluorescence, however both methods are limited or less desired because of isotope disposal issues and/or poor analytical resolution, sensitivity, and/or signal stability.

RLS particles provide a tool for analyzing and understanding small fluid volume deposition and dynamics on glass slides during array generation. Individual RLS particles can be seen using simple instrumentation to obtain an appropriate level of magnification. For pin transfer, where there is generally direct contact between the pin that carries the fluid held by surface tension and the slide surface upon deposition, distribution of fluid and the probe contained therein is rarely uniform. Furthermore, the distribution of probe frequently changes with drying as local sub-regions within the deposited fluid rapidly form. This effect causes non-uniform distribution of probe across the spot area. As such, the behavior of the probe across different areas of the spot is inconsistent during hybridization. This effect also can cause spot instability or "flaking" as areas of the spot that dry last generally have high levels of salt and probe, creating areas of differential binding on the slide. Different glass surface modifications and/or drying conditions either partially reduce or exacerbate this effect. The effects of specific conditions or changes can be determined using RLS particles, which may, for example, be attached to probe before or after deposition.

Other spotting methods are somewhat improved with respect to probe distribution since no contact pin is used to immediately establish liquid distribution differences upon deposition. Nevertheless, current methods do not allow one to examine, with a high degree of resolution, the parameters associated with spotting and drying and probe distribution that may still occur to some level with syringe-solenoid and piezoelectric deposition. Apart from this, there are other issues related to volume uniformity and port clogging in these two approaches in different applications. In this case, RLS particles are useful in developing formulations for spotting that affect uniform drying and improved drying dynamics, in conjunction with determination of the appropriate substrate surface properties to establish optimal assay performance. Typically, glass, silicon, or plastic substrates are used with a variety of surface chemistries including but not limited to amino, aldehyde, carboxylic acid, thiol, and functionalized silanes. RLS particles can also be used to determine the distribution of "functional" or hybridizing probe to its specific target under defined conditions. This aspect provides a method for not only determining the physical distribution of probe (nucleic acid, protein or any molecular component of a binding pair or complex) within the deposited area, but also the operational performance of the probes across the array feature.

RLS particles are also valuable tools for design, development and implementation of an arraying device. This is particularly the case with respect to pin, syringe or piezoelectric jet head design and quality control of pin manufacturing and performance. The ability to observe small fluid volumes and fluid dynamics using RLS particles is also important for developing robotic and fluid handling systems for reproducibly generating microarrays.

As indicated throughout the present description, the present methods are useful in many different applications. In the specific example of array production, exemplary system and process parameters that can be evaluated using RLS particle detection include, for example, spotting buffer formulation, pin selection, probe concentrations, relative humidity, post-spotting treatment, probe/feature stability to various experimental steps, and the like. These and other parameters can all be monitored in functional system development assays with a high level of resolution.

In connection with the use of light scattering particles for improving array drying parameters, an example is provided by the deposition of gold particle spots (e.g., 3 mm diameter) on glass slides coated with a gold particle binding agent. Careful observations were made of the manner in which water evaporates from the spot and the effect that this evaporation has on the final spatial distribution of particles in the spot. Initially, evaporation occurs at the periphery of the spot, causing a current of particles to the periphery resulting in the deposition of particles in an intense ring at the periphery. These rings are often seen in microarrays from different companies, indicating that this evaporation pattern also occurs when DNA probes are deposited in microspots. As evaporation proceeds, the particle current to the periphery ceases and a new current causes the particles to concentrate in a halo that is positioned between the periphery and the center of the spot. As total evaporation is approached, the halo concentrates on a spot which results in an intense area of particles in the final spot. This type of nonuniform pattern was also detected in commercial DNA chips that were examined, indicating that the deposition of DNA probes by evaporation results in DNA probe patters similar to the ones observed with RLS particle depostion.

Evaporation can be prevented by use of a humid chamber. In this case, the deposition of particles is diffusion dependent. Since diffusion is very slow, it takes overnight incubation and this still does not guarantee uniform spots. Thus, evaporation seems to be the best method for quickly bringing down the particles to a the glass surface. In order to improve the drying process to provide better uniformity across individual spots, a series of process modifications were performed and the effects tested using light scattering particles.

Studies on the evaporation process led to the idea that uniform spots might be obtained with use a two solvent system, one which evaporates rapidly (e.g., water) and the other (e.g., DMSO) which evaporates more slowly. Rapid evaporation of one of the solvents results in particles in a very thin film of the second solvent. In this thin film, particles can reach the surface by diffusion in a short time. While the use of a two solvent system improves uniformity, the distribution of gold particles in a spot is not always completely uniform.

In further experiments, a polymer was added gelatin to the two-solvent system as an agent for binding gold particles to the glass surface; with this addition, the spots were very uniform. It appears that as the first solvent evaporates, the polymere is concentrated into a viscous gel in the second solvent and that this inhibits particle currents. The particles thus maintain a uniform distribution in the second solvent and deposit on the surface in a uniform pattern. In an example using 80 nm gold particles with Ficoll, spots with uniform gold particle spatial distributions were obtained, but the particles had an orange light scattering color instead of the usual green light scattering color of 80 nm gold particles in air. However, after removing the Ficoll by washing, the spots displayed the expected green light scattering color.

Closer examination of the process revealed still further improvements. The washing process was examined in more detail by adding a small volume of water to the spot while viewing the spot in a dark field microscope. Observation revealed that many of the particles came off during washing. It appears that if the Ficoll concentration is high, many of the particles are trapped within the Ficoll gel matrix and not actually attached to the glass surface. However, within a certain low Ficoll concentration range, the spots are uniform and very few particles come off the spot during the washing step.

The process just described illustrates the application of the present methods for selecting materials, optimizing concentrations of materials, and improving process steps, resulting in improved spot uniformity.

A further illustration is directed to buffer selection, e.g., for selecting buffers for a washing step in an assay. In immuno and DNA probe assays on solid surfaces, the ability to see individual particles was very helpful in developing buffers with which to remove background non-specifically bound particles without affecting the specifically bound particles. On initial exposure of the solid phase to particle solution, typically a large number of particles become non-specifically bound to the solid phase material and/or to material bound on a sample spot. Indeed, in some cases, the surface concentration of non-specifically bound particles can exceed that of specifically bound particles, apparently due to electrostatic effects. In order to select a buffer solution, the relative effects of candidate buffers on the non-specifically bound particles and specifically bound particles can be compared. While viewing an RLS labeled spot, buffer is added. By looking at individual particles, the relative effects of the buffer on particles on the spots versus particles in the surrounding background areas can be determined. As indicated, those effects can then be compared for different buffers. This approach can similarly be applied to different types of solutions and solution components, e.g., relating to binding, reaction, washing, and/or detection steps.

A particular example of the utility of these methods relates to determination of the surface distribution of functional immobilized oligonucleotide capture probes on a solid phase surface. In this application, RLS particles directly or indirectly attached to complementary molecules are used to locate and gauge the distribution of functional (able to efficiently hybridize) probes after spotting and experimental processing. One can easily see and quantify the distribution and uniformity of functional probes resulting from a particular experimental protocol to minimize deleterious effects of small-volume drying, local salt gradients, crystallization, and the like.

In connection with production and use of arrays (and other device or assay formats that involve some form of binding of molecules (e.g., biomolecules such as nucleic acids and polypeptides) to solid phase surfaces, methods for labeling molecules such as nucleic acids and/or other biomolecules for analysis are numerous, but generally fall into two broad categories known as direct and indirect labeling.

For direct labeling, RLS particles can replace fluorescent tags and/or radioisotopes, and be incorporated directly into nucleic acids and/or polypeptides and/or other biomolecules. In this case, the particles are directly attached to the molecule of interest, e.g., attached to a nucleoside triphosphate or analog thereof and incorporated in an oligonucleotide. The RLS particle labeled nucleic acids and/or other molecules can be distributed onto a solid surface, such as microarray chips. The number and distribution of the RLS particles is an indicator of the number, distribution, and homogeneity of the deposited nucleic acids and/or other biomolecules. Such distribution and homogeneity can then be detected using the RLS particles as described, preferably using simple instrument, or even by eye with appropriate magnification.

For indirect labeling, the RLS particle labeled molecule, e.g., nucleic acids and/or other biomolecules, can also be used as probes for detecting a molecule or molecules of interest. In general, such probes utilize specific binding pair interactions. Common examples are in hybridization or binding assays. In these cases, the determination of RLS signals indicates the distribution of functional biomolecules selectively interacting with the probes. RLS particles can be associated with probe molecules in various ways (also applicable to associating RLS particles with molecules of interest). Typically the RLS particles are either indirectly associated with probe biomolecules such as nucleic acids or antibody probes through hapten binding effected by hapten incorporated into the probes, or by directly coupling the probes to the RLS particles. Hapten is incorporated into probe by either enzymatic or chemical labeling, and subsequently RLS particles coated with streptavidin or antibodies or other molecules that specifically bind to the introduced hapten are attached to the probe. Alternatively, as indicated, specific probes can be directly coupled to RLS particles by attaching the nucleic acid, antibody, or other biomolecule probes to the surface of RLS particles. In addition, RLS particles can be directly introduced into nucleic acid probes by incorporation labeling in the presence of the appropriate ribo- or deoxyribonucleoside triphosphate-derivatized RLS particles.

Dispensing and Mixing of Micro Volumes

RLS particles can also play an important role in development of instruments and optimization of methods for micro-dispensing fluids. This use may become especially important as combinatorial chemical synthesis moves toward miniaturization in concert with emerging low volume high throughput screening approaches (HTS) (e.g., 1564, 3456 and 9600 well formats). With respect to HTS, RLS particles are useful to optimize procedures associated with micro-volume reagent introduction and mixing.

The demonstrated ability to visualize individual RLS particles under high magnification using RLS microscope detection instrument establishes the usefulness of the present methods in small volume device and process development, testing, and quality control. One can easily distinguish by eye individual particles both in solution undergoing Brownian motion and as single particles immobilized to solid phase. This simple observation can be done, for example, by taking uncoated RLS particles bearing a net negative surface charge and spotting dilute solutions onto poly-lysine coated microscope slides. This same type of experiment has been done in solution using different sizes of RLS gold particles. In this case, one cannot only see individual particles distinctly, but the different colors and intensities can also be observed.

In a particular application, numerous experiments have been conducted using RLS particles to optimize spotting of nucleic acids for making microarrays. Throughout these experiments, uniformity of distribution of probes on a microarray feature and resulting signal was an emphasis. Indeed the ability to observe the signal on features in fine detail has also been conducted using many different systems using RLS particle detection. Most microarray spots developed without this important tool and process development advantage are more likely to be of significantly poorer quality, because of the limited ability to monitor and develop optimal equipment and processes. This has been noted in evaluation of cDNA and PCR product arrays spotted on glass slides as well as for many other array systems. RLS particles have also been used to examine the effect of different drying conditions on capture probe distribution and uniformity.

With regard to microfluidics, similar observations regarding individual particle detection have been made and applied. In one type of experimental demonstration, RLS particles were run through a micro-channel device by passive capillary action and detected using the RLS microscope instrument. Under these conditions, one can clearly see individual particles suspended in flow. Further, one can observe differential flow rates of individual particles as a function of channel position with respect to the channel wall. At cross-channel junctions, one can also readily observe RLS particles in flow into the cross channel at a reduced rate relative to the main component flow direction. One can quantitate component flow rates using real time analysis with conventional or high speed video camera linked to a personal computer and confinement analyzers and software.

Surface/Matrix Characterization

RLS particles can also be used to examine and/or quantitate various surface characteristics of solid surface substrates, and matrix properties of membranes and other porous substrates. Such characteristics and properties include but are not limited to physical, chemical and/or electrical properties such as flatness, texture, porosity, surface charge, surface charge uniformity, hydrophobicity, hydrophilicity, and chemical reactivity in addition to other properties. One of ordinary skill in the art will appreciate the utility of a small, stable, highly intense, particulate label, the surface of which can be systematically configured to provide multiple distinct properties, to interrogate and quantify label interaction with the substrate surface or matrix.

For example, the charge properties of a substrate surface can be examined by treating the surface with RLS particles having a distinct net surface positive or negative charge under conditions of low ionic strength. Such RLS particles may be prepared by coating the surface of the RLS particles with different mixtures of charged and/or non-charged polymers such at poly-lysine (positively charged polymer), polyethylene glycol (charge-neutral polymer) and/or a polymer of acrylic acid (negatively charged polymer). After treatment of the substrate surface with surface-charge-modified RLS particles under conditions that affect particle-substrate binding through charge-charge interaction, one can quantitate the uniformity of the charged substrate surface by quantitating the number and distribution of RLS particles on the surface. This would most typically be done at high resolution under dark field illumination conditions using a microscope instrument fitted with a CCD camera coupled to image and statistical analysis software to facilitate quantification of RLS particles on the substrate surface.

As another example, uniformity of distribution of reactive groups on a surface or in a porous substrate (e.g., a functionalized surface) can be determined by selecting a chemically appropriate molecule and reacting it with the reactive groups. The chemically appropriate molecule is additionally selected to provide binding to a moiety linked or linkable to RLS particles. As an example, the molecule reacted with the surface can provide a binding site for an antibody that is then recognized by a second antibody attached to an RLS particle. Numerous other binding arrangements can also be used. The number and/or distribution of bound RLS particles is then determined, and used as an indication of the number and/or distribution of functional groups on the surface or matrix.

Such approaches are particularly useful for analysis and quality control of various glass or plastic substrates which may have been modified using functionalized silanes, polymers, three dimensional matrices or porous materials to enhance binding of molecules to the substrate surface. Similar approaches can be applied to examine properties of membrane or other porous substrates related to function or performance in various applications including binding of molecules. One can also use RLS particles to examine the changes in substrate surface or porous matrix properties as a function of processing the substrate or matrix through one or more steps in an experimental procedure. For example, the effect on various properties with treatment of a solid glass or plastic substrate with heat, high salt buffers, organic solvents, blocking agents, detergents, in addition to other treatments, can be monitored using RLS particles.

EXAMPLES

Example 1
Preparation of a 16 nm Gold Particle Suspension 2.5 ml of sterile water was added to 0.1 g $HAuCl_4.3H_2O$ to form a 4% $HAuCl_4.3H_2O$ solution. The solution was centrifuged to remove particulate matter. In a separate flask, 10 ml of sterile water was added to 0.1 g. of sodium citrate to form a 1% sodium citrate solution. The citrate solution was filtered through a 0.4 µm polycarbonate membrane filter to remove particulate matter. To a very clean 250 ml Erlenmeyer flask, 100 ml of sterile water and 0.25 ml of the 4% $HAuCl_4.3H_2O$ was added. The flask was placed on a stir hot plate at a setting of 4 and covered with a 100 ml beaker. When the mixture started boiling, 2 ml of the 1% sodium citrate was added. The mixture solution was boiled for 30 more minutes and then cooled to room temperature and sterile water was added to bring the total volume to 100 ml. The final gold concentration is about 0.005% and particle concentration is $1.2 \times 10^{12}$ particles/ml, assuming that all the gold salt was converted to gold particles.

Example 2
Stabilization of Metal Particles with Polyethylene 1 gram of PEG (MW 20,000) was added to 100 ml of sterile water to form a 1% PEG solution and the solution was filtered through a 0.4 µm polycarbonate filter using a 50 ml syringe. To stabilize a given volume of particles, the volume of particle solution was added to a volume of 1% PEG solution that gives a final PEG concentration of 0.1%.

Example 3
Preparation of 30 nm Silver Coated Particles from 5 nm Diameter Gold Particles 10 ml of sterile water was brought to a boil in a 30 ml beaker. 2 mg of gelatin was then added slowly and the solution was allowed to continue to boil with stirring until all of the gelatin was dissolved. The solution was then cooled to room temperature. 2 ml of a 47% citrate buffer pH 5 was added. 0.18 ml of a solution containing 5 nm gold particles (at a concentration of about 0.005% gold, $3.8 \times 10^{13}$ gold particles/ml) was added followed by the addition of 3 ml of a 5.7% hydroquinone solution. The mixture was mixed well, followed by addition of sterile water for a final volume of 20 ml. 50 µl of a 4% silver lactate solution was added in 10 µl increments and the mixture was stirred rapidly by hand. The final silver concentration is about 0.005% and the final silver coated particle concentration was about $3.4 \times 10^{11}$ particles/ml. Assuming that all of the added silver had deposited equally on each gold particle, the particle size was calculated to be 30 nm. After the final addition, the sol appeared bright yellow in room lights. In bulk solution, the light scattered by a diluted volume of the sol contained in a 6×50 mm glass tube was blue when illuminated by a narrow beam of white light. When a dilution of the silver sol was examined microscopically with an RLS microscope instrument through a 10× objective and 12.5 eyepiece, a mixture of bright particles with different colors could easily be seen. The particles dominant in number were purple-blue particles. Yellow, green and red particles were also present. By adjusting the concentration of the 5 nm diameter gold particles used in the procedure described here, many sizes of silver coated particles can be made, e.g., with diameters in the range 20 to 100 nm.

Example 4
Preparation of Larger Diameter Gold Particles from 16 nm Diameter Particles A 2.4% solution of hydroxylamine hydrochloride was made by adding 24 mg. of hydroxylamine hydrochloride to 1 ml of sterile water, mixing and then filtering through a 4 μm polycarbonate membrane filter attached to a 10 ml syringe. A solution of 4% $HAuCl_4.3H_2O$ was made by adding 2.5 ml of sterile water to 0.1 g $HAuCl_4.3H_2O$ in a test tube mixing and then centrifuging to remove particulate matter. 25 ml of sterile water was added to a 250 ml Erlenmeyer flask, followed by addition of the volume of 16 nm gold particles shown in Table 1 depending on the desired particle size. Next the volume of the 4% $HAuCl_4.3H_2O$ solution specified in Table 1 was added. Finally sterile water was added to bring the total volume to 100 ml. Then the volume of the hydroxylamine hydrochloride solution specified in Table 1 was added with rapid hand stirring and the mixture was allowed to sit for 30 minutes. Within seconds after adding the hydroxylamine hydrochloride solution, the solution turned from a clear, slightly pink color to a final clear red or murky brown color, depending on particle size. The smaller sizes give red colored solutions.

TABLE 1

| Desired Au Particle Diameter, nm | 16 nm Gold Sol, ml | $HauCL_4.3H_2O$ Solution, ml | Hydroxyl-amine Solution ml |
|---|---|---|---|
| 40 | 6.4 | 0.234 | 1.25 |
| 60 | 1.9 | 0.245 | 1.25 |
| 80 | 0.8 | 0.248 | 1.25 |
| 100 | 0.41 | 0.249 | 1.25 |

Larger diameter particles were prepared following the same procedure as described above, but using the specified volumes of solutions as described in Table 2 and using the 100 nm diameter gold (Au) particle solution instead of the 16 nm gold solution.

TABLE 2

| Desired Au Particle Diameter, nm | 16 nm Gold Sol, ml | 4% $HauCl_4.3H_2O$ Solution, ml | Hydroxylamine Solution ml |
|---|---|---|---|
| 200 | 12.5 | 0.219 | 1.25 |
| 400 | 1.56 | 0.246 | 1.25 |
| 600 | 0.436 | 0.249 | 1.25 |
| 800 | 0.195 | 0.25 | 1.25 |
| 1000 | 0.1 | 0.25 | 1.25 |
| 2000 | 0.012 | 0.25 | 1.25 |

Example 5
Preparation of a Silver Coated Particle from 16 nm Gold Particles 25 ml of sterile water was added to a 250 ml Erlenmeyer flask followed by the addition of 6.4 ml of a 0.005% 16 nm gold particle sol and the resulting solution was mixed. 0.234 ml of a 40 mg/ml L(+) Lactic Acid silver salt solution was then added. A deep purple color was immediately seen. Enough sterile water was then added to bring the total volume to 100 ml. While rapidly stirring by hand, 1.25 ml of a 24 mg/ml solution of Hydroxylamine Hydrochloride was added and the resulting sol appeared lavender silver in color. A small drop of the sol was placed on a glass slide, covered with a cover glass and examined with an RLS microscope instrument. Red, green, purple, and yellow particles were seen. The scattered light color of a dilute solution of these particles in a test tube with white light illumination was ice blue.

Example 6
Field Flow Fractionation Design and Fabrication

Field Flow Fractionation (FFF) systems can be made in both Macro or Micro formats. Macro systems typically have channels 30–60 cm in length, a height of around 130 μm, and a width of 2 cm. (B. K. Gale, K. D. Caldwell, A. B. Fraiser, "A Micromachined Electrical Field-Flow Fractionation (μEFFF) System, *IEEE Transactions on Biomedical Engineering*, Vol 45, No 12, pp. 1459–1468, December 1998). Macro systems are large enough to be manufactured through traditional processes such as plastic injection molding, and film lamination of clear plastics such as polystyrene, polycarbonate, acrylic and mylar.

Micro devices manufactured through micromachining are typically 6 cm in length, 8 mm in width and 10–30 μm in height. Both Macro and Micro systems generally utilize width to height ratios of channel dimensions of greater than 100:1 to minimize edge effects, approximating flow between two infinite parallel plates. Micro devices are typically fabricated with silicon or glass substrates, and can be patterned with vacuum deposited electrodes for manipulation and detection of the fluid within the channel electrically. These electrodes can be pure metals such as gold, tin or platinum, or alloys such as indium-tin oxide. Micro FFF devices are manufactured with semiconductor process such as photolithography using "spin on" polyamide coatings over the substrate, such as SU8 epoxy to create the space for the channels. Individual components or the entire channel may be coated with a wetting agent or surfactant to change the fluid dynamics of the channel. Coatings may also be used to provide biocompatibility between the device and sample. Those skilled in the art are familiar with various coatings and methods of coating.

There are a number of different types of FFF systems based on the type of forces or fields applied across the channel from top to bottom. This force results in the fractionation of particles of different size or charge density. These forces can be applied by temperature gradients, sedimentation (both gravitational and centrifugal), cross-flow, magnetic, and particle charge density (electrical). Fluid flow along length is typically accomplished using a small peristaltic or syringe pump with a flow rate controller, however, capillary flow systems have also been developed. Flow rates for FFF systems are determined by the desired resolution, channel dimensions and the force being applied. Normal operating flow rates are typically 1 cm/sec and lower.

Light scattering particles can be utilized in the design and manufacture of FFF systems, for example, to analyze fluid flow within the device, separation patterns, manufacturing quality control, and flow into and out of the device.

Example 7
Detection of RLS Particles in a Microchannel

This example demonstrates the detection of light scattering particles in a microchannel device, but is demonstrative of similar detection in a variety of different types of devices.

0.05 μL of 80 nm anti-biotin coated gold RLS particles (1:10 mixture of 5OD particles:DI water), were injected into a flat, glass microchannel having clear top and bottom surfaces, a cross-sectional area of $1.25 \times 10^{-3}$ cm$^2$ (25 μm×5.0 mm), length of 500 mm, and a total volume equal to $7.5 \times 10^{-3}$ mL. The carrier fluid was deionized water with a flow rate of 0.6 mL/hr (0.13 cm/s).

Light was provided by a trans-illumination system using a focused polychromatic light source, directed to the channel through a prism optically coupled to the bottom of the channel arranged to provide dark field illumination. Particles in suspension were introduced into the microchannel, and flowed in the microchannel. Flow can be generated in a variety of ways, including a variety of force and capillary flow approaches. While this example utilized trans-illumination, epi-illumination has also been demonstrated in microchannel applications (and is applicable to a variety of other applications). Such epi-illumination (or other illumination technique with illumination and detection from the same side of the surface or device) can be used with transparent channels, or with channels (likewise for other types of microdevices) with only one transparent surface.

Figure 3:
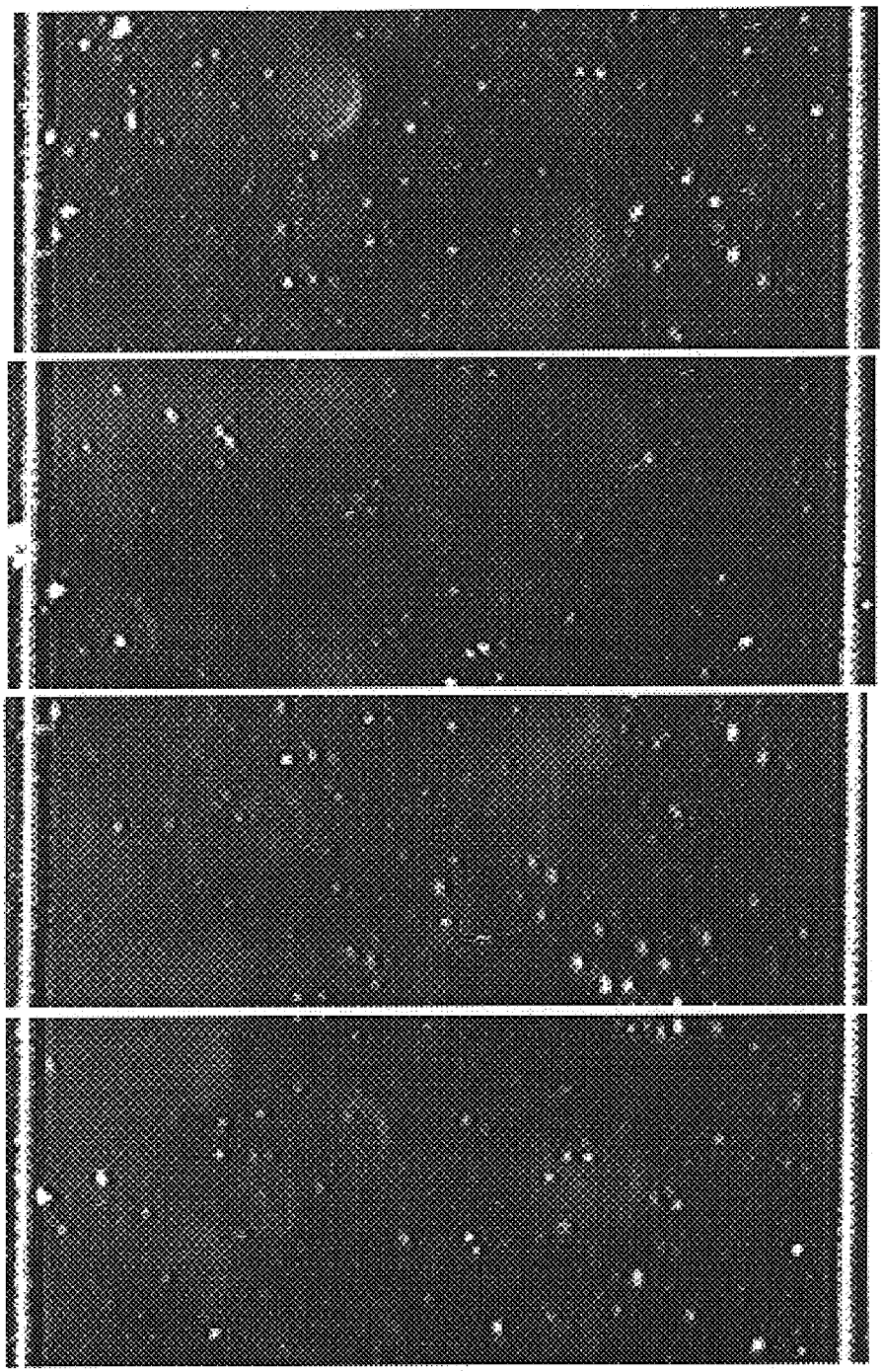
FIG. 3 shows four sequential images of light scattering particles flowing through a microchannel using dark field trans-illumination.

Images were acquired using a microscope objective-based viewing system fitted with a CCD video camera. Four time-lapse images are shown in FIG. 3, with the first image located at the top. The interval between images was 86 msec. The axis of the channel is oriented vertically in the images.

This example demonstrates that light scattering particles can be readily introduced and detected in microdevices. One of ordinary skill in the art will recognize that the detection can be readily adapted to a large variety of other microdevices of varying scale, as well as to many macrodevice applications.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art will readily appreciate that the present invention is well adapted to carry out the objects and obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, using other light scattering particles, and/or micro devices are all within the scope of the present invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms for other embodiments. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Where a component or limitation is described with a variety of different possible numbers or dimensions associated with that component or limitation, in additional embodiments, the component or limitation is in a range specified by taking any two of the particular values provided as the endpoints of the range. The range includes the endpoints unless clearly indicated to the contrary.

Thus, additional embodiments are within the scope of the invention and within the following claims.

What is claimed is:

1. A method for analyzing deposition characteristics of molecules of interest on a solid substrate, comprising:
    depositing at least one fluid volume on a portion of a solid substrate, wherein said fluid volume comprises the molecules of interest and a plurality of light scattering particles, and wherein said molecules of interest do not bind specifically to said light scattering particles; and
    detecting the distribution or number or both of said light scattering particles by detecting light scattered from said particles,
    wherein the distribution or number or both of said particles is indicative of one or more deposition characteristics of said molecules of interest on said solid substrate.

2. The method of claim 1, wherein said solid substrate comprises one or more discrete areas, wherein said deposition characteristic is uniformity of deposition, and wherein said uniformity is evaluated by determining at least one of the properties selected from the group consisting of a two-dimensional distribution of particles within at least one discrete areas of said solid substrate, deposition volume, and uniformity of particle number in deposited fluid volumes.

3. The method of claim 1, wherein said deposition characteristic is a drying pattern.

4. A method for analyzing deposition characteristics of molecules of interest on a solid substrate, comprising
    depositing on a portion of a solid substrate at least one fluid volume that comprises a plurality of light scattering particles, wherein said molecules of interest are present on said portion of said solid substrate, and wherein said light scattering particles bind non-specifically to said molecules of interest; and
    detecting the distribution or number or both of said light scattering particles by detecting light scattered from said particles,
    wherein the distribution or number or both of said particles is indicative of one or more deposition characteristics of said molecules of interest on said solid substrate.

5. The method of method claim 1 or 4, wherein said distribution of interest is formed during drying of said fluid volume comprising said molecules of interest on said solid substrate.

6. The method of claim 1 or 4, wherein said distribution of said light scattering particles is formed during or after post-spotting processing of said fluid volume on said solid substrate.

7. The method of claim 1 or 4, wherein said solid substrate comprises at least 10, 100, 1000 or 10,000 discrete areas.

8. The method of claim 7, wherein said discrete areas comprises at least one feature selected from the group consisting of a flat surface, a well and a channel.

9. The method of claim 7, wherein said solid substrate is a glass substrate, a functionalized glass substrate, a plastic substrate, a silicon substrate, a membrane substrate, a metallic substrate, a polystyrene substrates, a polymer substrate or some combination thereof.

10. The method of claim 7, wherein said solid substrate is a part of a device, a microscale device, a nanoscale device, an array, a microarray, an array chip, an array plate or an array slide.

11. The method of claim 7, wherein said molecules of interest are selected from the group consisting of nucleic acids, proteins, peptides, antibodies, ligands, receptors or polypeptides.

12. The method of claim 4, wherein said solid substrate comprises one or more discrete areas, wherein said deposition characteristic is uniformity of deposition, and wherein said uniformity is evaluated by determining at least one of the properties selected from the group consisting of a two-dimensional distribution of particles within at least one discrete areas of said solid substrate, deposition volume, and uniformity of particle number in deposited fluid volumes.

13. The method claim 4, wherein said deposition characteristic is a drying pattern.

14. The method of claim 1 or 4, wherein said at least one fluid volume is a small volume, a microvolume, a nanovolume, or a picovolume.

15. The method of claim 1 or 4, wherein said at least one fluid volume is deposited by at least one means selected from the group consisting of piezoelectric means, inkjet, solenoid/piston means, and pin transfer means.

16. The method of claim 1 or 4, wherein said plurality of light scattering particles comprise more than one different, separately distinguishable populations of light scattering particles.

17. The method of claim 1 or 4, wherein a binding of said molecules of interest to a target comprises nucleic acid hybridization, protein-protein interaction, ligand-receptor binding, or antibody binding.

18. The method of claim 1 or 4, further comprising a step of drying said fluid volume prior to said detecting step.

19. A method for analyzing at least one characteristic of a solid or porous substrate, comprising
treating at least a portion of a sample of said substrate with at least one fluid volume containing a plurality of light scattering particles; and
detecting the distribution or number or both of said light scattering particles on said at least a portion of said sample by detecting light scattered from said particles, wherein the distribution or number or both of said particles is indicative of said at least one characteristic of said solid or porous substrate.

20. The method of claim 19, wherein substrate is a solid substrate and said characteristic is a surface characteristic.

21. The method of claim 19, wherein said substrate is a porous matrix.

22. The method claim 20, wherein said at least one characteristic is selected from the group consisting of surface uniformity, uniformity of one or more surface coatings, uniformity of surface charge, uniformity of surface hydrophilicity, uniformity of surface hydrophobicity, and uniformity of surface charge density.

23. The method of claim 19, wherein said substrate is selected from the group consisting of a glass substrate, a functionalized glass substrate, a plastic substrate, a silicon substrate, a membrane substrate, and a metallic substrate.

24. The method of claim 21, wherein said porous matrix is nitrocellulose, polyvinylidene fluoride, or nylon.

25. The method of claim 21, wherein said at least one characteristic is selected from the group consisting of matrix uniformity, uniformity of one or more coatings, uniformity of charge, uniformity of hydrophilicity, uniformity of hydrophobicity, and uniformity of charge density.

26. The method of claim 19, wherein said substrate comprises a silane, a polymer or a three dimensional matrix.

\* \* \* \* \*